(12) United States Patent
Neveu

(10) Patent No.: US 12,377,046 B1
(45) Date of Patent: Aug. 5, 2025

(54) DELIVERY SYSTEM MATRICES

(71) Applicant: Wellomics LLC, Bethel, ME (US)

(72) Inventor: Mark J. Neveu, Bethel, ME (US)

(73) Assignee: Wellomics LLC, Bethel, ME (US)

( * ) Notice: Subject to any disclaimer, the term of this patent is extended or adjusted under 35 U.S.C. 154(b) by 877 days.

(21) Appl. No.: 16/857,865

(22) Filed: Apr. 24, 2020

Related U.S. Application Data

(60) Provisional application No. 62/838,260, filed on Apr. 24, 2019.

(51) Int. Cl.

| | | |
|---|---|---|
| *A61K 31/7008* | (2006.01) | |
| *A23B 20/10* | (2025.01) | |
| *A23D 7/005* | (2006.01) | |
| *A23D 7/04* | (2006.01) | |
| *A23L 29/231* | (2016.01) | |
| *A23L 29/25* | (2016.01) | |
| *A23L 33/105* | (2016.01) | |
| *A23L 33/125* | (2016.01) | |
| *A23L 33/22* | (2016.01) | |
| *A61K 9/06* | (2006.01) | |
| *A61K 9/107* | (2006.01) | |
| *A61K 47/36* | (2006.01) | |

(52) U.S. Cl.
CPC .............. *A61K 9/107* (2013.01); *A23B 20/10* (2025.01); *A23D 7/0053* (2013.01); *A23D 7/04* (2013.01); *A23L 29/231* (2016.08); *A23L 29/25* (2016.08); *A23L 33/105* (2016.08); *A23L 33/125* (2016.08); *A23L 33/22* (2016.08); *A61K 9/06* (2013.01); *A61K 47/36* (2013.01); *A23V 2002/00* (2013.01)

(58) Field of Classification Search
CPC .......... A61K 9/06; A61K 9/107; A61K 47/36; A23L 29/231; A23L 29/25; A23L 33/105; A23L 33/125; A23L 33/22; A23D 7/0053

USPC ........................................................ 514/777
See application file for complete search history.

(56) References Cited

U.S. PATENT DOCUMENTS 5,630,796 A  5/1997  Bellhouse et al.

FOREIGN PATENT DOCUMENTS

| JP | 6836825 B2 | 3/2021 | |
|---|---|---|---|
| WO | WO 2013/149323 A1 * | 10/2013 | ............... A61K 8/97 |
| WO | WO 2017/009480 A1 | 1/2017 | |

OTHER PUBLICATIONS

Maier et al., Food Hydrocolloids, 2016, 57, 221-228.*
Chan et al, Carbohydrate Polymers, 2017, 161, 118-139.*
Mayuree et al, Polysaccharides, 2015, pp. 1867-1892, Springer International Publishing.*
Abel et al., Stimulation of human monocyte beta-glucan receptors by glucan particles induces production of TNF-alpha and IL-1 beta. Int J Immunopharmacol. Nov. 1992;14(8):1363-73. doi: 10.1016/0192-0561(92)90007-8.
Yu et al., Tunable glycyrrhizic acid supramolecular hydrogels via metal ion complexation. Giant. 2024; 17: 1-15. https://doi.org/10.1016/j.giant.2024.100240.

* cited by examiner

*Primary Examiner* — Ganapathy Krishnan
(74) *Attorney, Agent, or Firm* — Wolf, Greenfield & Sacks, P.C.

(57) ABSTRACT

This invention relates to delivery matrix compositions (e.g., dietary products or pharmaceuticals) and related methods. In particular, the disclosure relates to delivery matrix compositions that include temperature-dependent O/W emulsion complexes, low viscosity sheared fluid gels, and viscous hydrogels that can facilitate the delivery of a wide range of substances to the gastrointestinal tract (e.g., small intestine) of a subject.

26 Claims, 1 Drawing Sheet

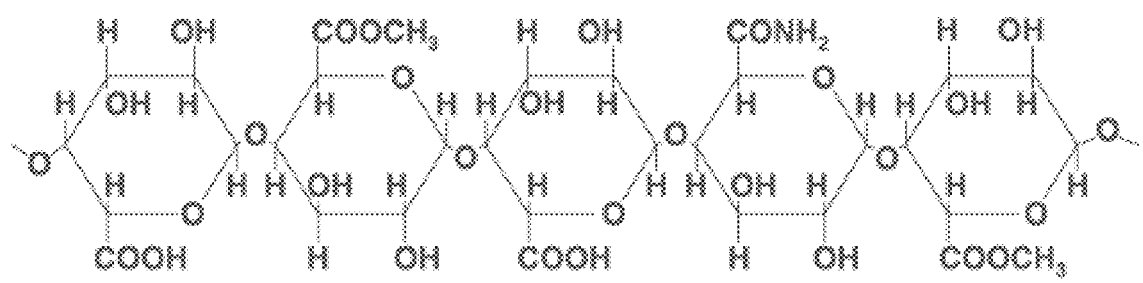
AMIDATED LOW ESTER PECTIN

DELIVERY SYSTEM MATRICES

RELATED APPLICATIONS

This application claims the benefit of priority under 35 U.S.C. § 119 of U.S. provisional application 62/838,260, filed Apr. 24, 2019, the entire contents of which is incorporated herein by reference.

FIELD OF THE INVENTION

This invention relates to delivery matrix compositions (e.g., dietary products or pharmaceuticals) and related methods. In particular, the disclosure relates to delivery matrix compositions that include temperature-dependent hydrogel O/W emulsion complexes, low viscosity sheared fluid microgels, and viscous hydrogels that can facilitate the targeted delivery of a wide range of bioactive substances to various segments of the gastrointestinal tract (e.g., small intestine) of a subject. Any of the compositions provided herein can be natural vegan (e.g., non-GMO, non-soy, allergen free) compositions.

SUMMARY OF THE INVENTION

In one aspect, an oil-in-water (O/W) emulsion complex comprising a water phase and an oil phase, wherein the water phase comprises an ascorbyl palmitate (e.g., amphipathic water-insoluble ascorbyl palmitate), a high hydrophile-lipophile balance (HLB) saponin (e.g., anionic), and a *Glycyrrhiza glabra* (licorice) root saponin is provided.

In one embodiment of any one of the compositions or methods provided herein, the high HLB saponin is a *Quillaja saponaria* saponin (e.g., extract). In one embodiment of any one of the compositions or methods provided herein, the high HLB saponin is a *Yucca* saponin (e.g., extract). In one embodiment of any one of the compositions or methods provided herein, the high HLB saponin (e.g., emulsifier or co-emulsifier) is from tea seeds, bitter melon *Momordica charantia, Panax ginseng*, fenugreek *Trigonella Foenum graecum*, alfalfa root *Medicago sativa*, Siberian ginseng *Eleuthrerococcus senticosus, Astragalus membranaceus, Bacopa monniera, Nigella sativa, Aralia mandshurica, Beyonia alba, Rhaponticum carthamoides, Gymnema sylvestre, Gynostemma pentaphyllum, Withania somnifera, Tinaspora cordifolia*, Milkwort Polygala, *Simlax officinalis*, or *Aesculis hipocastanum*, or a natural sourced saponin (e.g., bacterial) or emulsifier (e.g., *stevia*, monk fruit).

In one embodiment of any one of the compositions or methods provided herein, the *Glycyrrhiza glabra* (licorice) root saponin is monoammonium glycyrrhizinate, ammoniated glycyrrhizin, or glycyrrhizic acid.

In one embodiment of any one of the compositions or methods provided herein, the oil phase comprises an edible oil.

In one embodiment of any one of the compositions or methods provided herein, the water and/or oil phase further comprises an antioxidant.

In one embodiment of any one of the compositions or methods provided herein, the O/W emulsion complex further comprises a stabilizing hydrophilic agent.

In one embodiment of any one of the compositions or methods provided herein, the O/W emulsion complex further comprises a compound that increases bioavailability.

In one embodiment of any one of the compositions or methods provided herein, the O/W emulsion complex further comprises a viscosity modifier. In one embodiment of any one of the compositions or methods provided herein, the viscosity modifier is a humectant or mucilaginous ingredient.

In one embodiment of any one of the compositions or methods provided herein, the concentration of ascorbyl palmitate is 0.15-4.5 mg/gm. In one embodiment of any one of the compositions or methods provided herein, the concentration of the high HLB saponin is 0.01-1.6 mg/gm. In one embodiment of any one of the compositions or methods provided herein, the concentration of *Glycyrrhiza glabra* root saponin is 0.02-160 mg/gm.

In one embodiment of any one of the compositions or methods provided herein, the O/W emulsion complex is thixotropic. In one embodiment of any one of the compositions or methods provided herein, the O/W emulsion complex has a glass-transition temperature range between 50-80° C.

In one embodiment of any one of the compositions or methods provided herein, the O/W emulsion complex further comprises a dietary agent. In one embodiment of any one of the compositions or methods provided herein, the O/W emulsion complex further comprises a pharmaceutical agent. In one embodiment of any one of the compositions or methods provided herein, the O/W emulsion complex comprises a dietary agent and a pharmaceutical agent.

In one aspect, a fluid gel (e.g., microgel) delivery matrix comprising:
  (a) an O/W emulsion complex (e.g., anionic or anionic hydrogel);
  (b) a low ester pectin; and
  (c) a cation is provided.

In one embodiment of any one of the compositions or methods provided herein, the O/W emulsion complex is any one of the O/W emulsion complexes provided herein.

In one embodiment of any one of the compositions or methods provided herein, the low ester pectin is an amidated low ester pectin. In one embodiment of any one of the compositions or methods provided herein, the low ester pectin is a citrus peel or apple pectin. In one embodiment of any one of the compositions or methods provided herein, the low ester pectin has the structure as shown in FIG. 1.

In one embodiment of any one of the compositions or methods provided herein, the cation is a divalent cation. In one embodiment of any one of the compositions or methods provided herein, the divalent cation is a Calcium, Zinc, Magnesium, Manganese or other divalent cation(s). In one embodiment of any one of the compositions or methods provided herein, wherein the concentration of low ester pectin is 1.50-5.00 mg/gm.

In one embodiment of any one of the compositions or methods provided herein, the fluid gel delivery matrix further comprises an acidulant.

In one embodiment of any one of the compositions or methods provided herein, the fluid gel delivery matrix has a viscosity of 50-50,000 cps.

In one embodiment of any one of the compositions or methods provided herein, the fluid gel delivery matrix further comprises a dietary agent. In one embodiment of any one of the compositions or methods provided herein, the fluid gel delivery matrix further comprises a pharmaceutical agent. In one embodiment of any one of the compositions or methods provided herein, the fluid gel delivery matrix further comprises a dietary agent and a pharmaceutical agent.

In one aspect a hydrogel delivery matrix (e.g., viscous hydrogel delivery matrix) comprising:

a fluid gel delivery matrix (e.g., microgel) or an O/W emulsion complex (e.g., hydrogel);

at least one beta glucan; and (a) any one or more of acacia gum, a hydrocolloid, and a molecule that reduces syneresis and increases viscosity; and/or (b) a fructooligosaccharide and/or other a gut healthy fiber to improve nutrient bioavailability, target ingredients to specific areas of gastrointestinal tract, and/or promote healthy microbiome.

In an embodiment of any one of the compositions or methods provided herein, the composition may further comprise or the method may further comprise adding a divalent ion sensitive hydrocolloid (e.g., gellan gum, alginate, carrageenan), a cationic chitosan (e.g., shellfish and mushroom), a digestible or non-digestible hydrocolloid (e.g., locust bean gum), a gel-forming natural products (e.g., chondroitin, glucosamine, hyaluronate, fucoidan), or a combination thereof.

In an embodiment of any one of the compositions or methods provided herein, the molecule that reduces syneresis and increases viscosity is any one of such molecules described herein or otherwise known in the art. Such molecule may be a plant extract (e.g., Pregeflo®, Glucidex®, Perfectasol®, Solanic®, Risolubles®), dietary fiber (e.g., larch arabinogalactan, flax seed, fenugreek, psyllium, inulin, Sunfiber®, Orafti®, Oliggo®), protein (e.g., pea, potato, milk, soy), cyclodextrin (e.g., alpha, beta and gamma), beet pectin or a high methoxy calcium insensitive pectin in any one such embodiment.

In an embodiment of any one of the compositions or methods provided herein, the gut healthy fiber to improve nutrient bioavailability, target ingredients to specific areas of gastrointestinal tract, and/or promote healthy microbiome is any one of such molecules described herein or otherwise known in the art. Such molecule may be a mucilaginous extract (e.g., Aloe vera, lotus, okra, Mucosave®, Opunxia®), Astragin® extract, a hydrocolloid or dietary fiber that has distinct digestion profiles in different segments of the digestive system, etc. in any one such embodiment. Such molecule may also be an ingredient that binds specific receptors to enhance absorption in specific areas of the digestive system (e.g., chitosan and related cationic complexes that can deliver ingredients to the stomach) or a non-digestible calcium insensitive hydrocolloid that can delay small intestine absorption and target ingredients to the large intestine in any one such embodiment.

In an embodiment of any one of the hydrogel delivery matrices provided herein, the hydrogel delivery matrix further comprises other pH, salt, or gastrointestinal enzyme or cation responsive hydrocolloid (e.g., alginate, gellan, carrageenan).

In one embodiment of any one of the compositions or methods provided herein, the fluid gel delivery matrix is any one of the fluid gel delivery matrices provided herein.

In one embodiment of any one of the compositions or methods provided herein, the beta glucan is a cereal (e.g., oat), yeast, or mushroom beta glucan. In one embodiment of any one of the compositions or methods provided herein, the concentration of the beta glucan is 2.0-30.0 mg/gm.

In one embodiment of any one of the compositions or methods provided herein, the concentration of the acacia gum is 2.0-30.0 mg/gm.

In one embodiment of any one of the compositions or methods provided herein, the hydrogel has a viscosity of 10,000 to 100,000 cps.

In one embodiment of any one of the compositions or methods provided herein, the hydrogel delivery matrix further comprises a dietary agent. In one embodiment of any one of the compositions or methods provided herein, the hydrogel delivery matrix further comprises a pharmaceutical agent. In one embodiment of any one of the compositions or methods provided herein, the hydrogel delivery matrix further comprises a dietary agent and a pharmaceutical agent.

In one embodiment of any one of the compositions or methods provided herein, the delivery matrix further comprises a flavoring or a flavoring is added.

In one aspect are method for preparing any one of the delivery matrices provided herein. In one aspect a method of preparing an O/W emulsion complex, the method comprising:

(a) low shear mixing an oil phase, protected from light, at 42-100° C.;

(b) heating or maintain a water phase to/at 55-90° C. and mixing low shear;

(c) sequentially adding a high HLB saponin (e.g., anionic), *Glycyrrhiza glabra* (licorice) root saponin, and ascorbyl palmitate to the water phase; and (d) mixing the oil phase into the water phase at 55-90° C. with high sheer is provided.

In one embodiment of any one of the methods provided herein, the antioxidant is sequentially added to the oil phase in step (a) and/or the water phase in step (c).

In one embodiment of any one of the methods provided herein, the high HLB saponin, the *Glycyrrhiza glabra* (licorice) root saponin, and the ascorbyl palmitate are sequentially added to the water phase at a pH of between 3-5 and/or at a temperature of greater than 55° C. (e.g., greater than 55° C. but less than 95° C.). This can result in the solution turning transparent.

In one embodiment of any one of the methods provided herein, the method further comprises adding a dietary agent. In one embodiment of any one of the methods provided herein, the method further comprises adding a pharmaceutical agent. In one embodiment of any one of the methods provided herein, the method further comprises adding a dietary agent and a pharmaceutical agent.

In one embodiment of any one of the methods provided herein, the method further comprises (e) reducing heat and adding a composition comprising a pectin. In one embodiment of any one of the methods provided herein, the pectin is a low ester pectin. In one embodiment of any one of the methods provided herein, the low ester pectin is an amidated low ester pectin. In one embodiment of any one of the methods provided herein, the low ester pectin is a citrus peel or apple pectin. In one embodiment of any one of the methods provided herein, the low ester pectin has the structure as shown in FIG. 1.

In one embodiment of any one of the methods provided herein, a dietary agent is also mixed in any one of the steps or the method further comprises a step of mixing a dietary agent. In one embodiment of any one of the methods provided herein, a pharmaceutical agent is also mixed in any one of the steps or the method further comprises a step of mixing a pharmaceutical agent. In one embodiment of any one of the methods provided herein, a dietary agent and a pharmaceutical agent are also mixed in any one of the steps or the method further comprises a step of mixing a dietary agent and a pharmaceutical agent.

In one aspect, a method of preparing a fluid gel delivery matrix, the method comprising:
(a) preparing an O/W emulsion complex (e.g., hydrogel);
(b) hydrating a low ester pectin at 70-90° C. and allowing it to cool to room temperature;
(c) adding the hydrated low ester pectin at a high shear rate; and
(d) adding purified water at room temperature;
(e) reducing the temperature to 42° C.; and
(f) adding sequentially a dietary agent and/or pharmaceutical agent is provided.

In an embodiment of any one of the methods provided herein, the dietary agent and/or pharmaceutical agent is provided while maintaining a pH of between 3-5.

In an embodiment of any one of the methods provided herein, divalent cations (e.g., calcium and/or zinc) is added to induce gelation and complexation, such as of a O/W emulsion (e.g., hydrogel) to the pectin.

In one embodiment of any one of the methods provided herein, preparing an O/W emulsion complex comprises the steps of any one of the methods for doing so provided herein.

In one embodiment of any one of the methods provided herein, low ester pectin is an amidated low ester pectin. In one embodiment of any one of the methods provided herein, the low ester pectin is a citrus peel or apple pectin. In one embodiment of any one of the methods provided herein, the low ester pectin has the structure as shown in FIG. 1.

In one embodiment of any one of the methods provided herein, a dietary agent is also mixed in any one of the steps or the method further comprises a step of mixing a dietary agent. In one embodiment of any one of the methods provided herein, a pharmaceutical agent is also mixed in any one of the steps or the method further comprises a step of mixing a pharmaceutical agent. In one embodiment of any one of the methods provided herein, a dietary agent and a pharmaceutical agent are also mixed in any one of the steps or the method further comprises a step of mixing a dietary agent and a pharmaceutical agent.

In one aspect, a method of preparing a hydrogel delivery matrix, the method comprising:
(a) preparing a fluid gel delivery matrix or O/W hydrogel emulsion;
(b) adding, sequentially, (1) a beta glucan, and (2) any one or more of acacia gum, a hydrocolloid, and a molecule that reduces syneresis and increases viscosity and/or (3) a fructooligosaccharide and/or other a gut healthy fiber to improve nutrient bioavailability, target ingredients to specific areas of gastrointestinal tract, and/or promote healthy microbiome; and
(c) cooling the mixture to room temperature.

In an embodiment of any one of the methods provided herein, other pH, salt, or gastrointestinal enzyme or cation responsive hydrocolloid (e.g., alginate, gellan, carrageenan) are also added (e.g., sequentially).

In one embodiment of any one of the methods provided herein, the preparing a fluid gel delivery matrix comprises the steps of any method for doing so provided herein.

In one embodiment of any one of the methods provided herein, the method further comprises (d) adding a dietary agent. In one embodiment of any one of the methods provided herein, the method further comprises (e) adding a pharmaceutical agent. In one embodiment of any one of the methods provided herein, the method further comprises (d) adding a dietary agent and a pharmaceutical agent.

In one embodiment of any one of the methods provided herein, the method further comprises (f) adjusting the weight of the hydrogel with ddH$_2$O.

In one embodiment of any one of the methods provided herein, the beta glucan is a cereal (e.g., oat), yeast or mushroom beta glucan.

Provided herein are methods, compositions and kits related to such delivery systems. The methods, compositions or kits can be any one of the methods, compositions or kits, respectively, provided herein, including any one of those of the Examples.

In one embodiment, any one of the embodiments for the methods provided herein can be an embodiment for any one of the compositions, kits or reports provided. In one embodiment, any one of the embodiments for the compositions, kits or reports provided herein can be an embodiment for any one of the methods provided herein.

BRIEF DESCRIPTION OF THE DRAWINGS

FIG. 1 illustrates the structure of an exemplary amidated low ester citrus peel pectin that may be used in the formation of a fluid gel delivery matrix described herein.

DETAILED DESCRIPTION OF THE INVENTION

The majority of nutrients from the diet are absorbed into the blood across the mucosa of the small intestine. Likewise, the majority of drug absorption occurs in the small intestine, as the tract's large surface area and copious population of villi and microvilli increase the region's absorptive capacity significantly. Targeting delivery of dietary agents, including nutrient agents (e.g., vitamins, minerals, botanicals, natural products), and/or drugs directly to the site of absorption (small intestine) can be more efficient and/or have beneficial effects. For example, transit time in the small intestine is approximately four hours, whereas other sites of absorption, such as the large intestine, have much longer transit times (e.g., 6-70 hours). Targeted delivery to the small intestine can also decrease side effects and has the potential to maximize the potential efficacy of agents delivered. Therefore, aspects of the disclosure relate to compositions and methods relating to gastrointestinal delivery systems.

The present disclosure is based, at least in part on the discovery of deliver matrices that are natural and have beneficial properties, including those with one or more of the beneficial properties described herein. For example, provided herein are certain emulsion formulations that can protect ingredients from oxidation in a temperature-, concentration-, and/or pH-sensitive manner. In an embodiment, the emulsion complexes are oil-in-water (O/W) emulsion complexes that comprise anionic, water-insoluble ascorbyl palmitate, a high hydrophile-lipophile balance (HLB) anionic saponin, and an anionic *Glycyrrhiza glabra* (licorice) root saponin. It has been found that such O/W emulsion complexes can form a hydrogel. Without being bound by any theory, it has been found that the anionic, water-insoluble ascorbyl palmitate can form a hydrogel, the high HLB anionic saponin can form micelles, and the anionic *Glycyrrhiza glabra* (licorice) root saponin can form fibrillary gels when processed as provided herein.

In an embodiment, any one of the emulsion complexes provided herein can be for targeting the complete digestive system. In an embodiment, this can include the oral cavity. In another embodiment, any one of the gel compositions provided herein that comprise pectin can be for targeting the small intestine, as agent(s) can be protected from stomach acid and/or enzymes. In another embodiment, any one of the viscous hydrogels provided herein can be for targeting the large intestine, such as to promote gastrointestinal health, increasing lymphatic absorption, etc.

The delivery matrices provided herein can be for the delivery of complex natural products and/or pharmaceuticals and can utilize only natural vegan (e.g., non-gmo, non-soy, gluten and allergen-free) ingredients, in some embodiments. The delivery matrices can target different areas of the digestive system, in some embodiments. However, depending on formulation goals synthetic ingredients may be substituted.

Oil-in-Water Emulsion Complex

Generally, what is required for bioavailability is dissolution of the ingredients required for optimal absorption. The emulsion complexes provided herein can act similarly to bile/oil particles that are naturally formed during the digestive process and can greatly enhance bioavailability of hydrophobic agents.

"Emulsion complex" refers to a liquid mixture of the water phase and the oil phase. Emulsions are heterogeneous systems of two or more immiscible liquid phases, and may be produced from any suitable combination of immiscible liquids. The emulsions of the present disclosure comprise a hydrophobic, immiscible liquid (the oil phase) as the phase present in the form of finely divided droplets (the disperse, internal, or discontinuous phase) and a hydrophilic phase (the water phase) as the matrix in which these droplets are suspended (the non-disperse, continuous or external phase). Such emulsions are termed "oil-in-water" or "O/W".

The O/W complexes provided herein have beneficially been found to be able to form a hydrogel. A "hydrogel" as provided herein refers to a macromolecular polymer gel constructed of crosslinked polymer chains. Any one of the emulsion complexes provided herein can be a hydrogel.

In an aspect provided herein, the water phase of an emulsion complex can comprise a an anionic, water-insoluble ascorbyl palmitate, a high hydrophile-lipophile balance (HLB) anionic saponin and an anionic *Glycyrrhiza glabra* (licorice) root saponin (that can form a fibril gel). These components can also act as potent antioxidants to further protect the oil phase from oxidation.

In an embodiment of any one of the compositions and methods provided herein the ascorbyl palmitate can be sparingly soluble in water and provided in an anionic lamellar liquid crystal form. The ascorbyl palmitate can form hydrogel structures, such as following a cycle of heating and cooling. The ascorbyl palmitate may be at a concentration of 0.15-4.5 mg/gm in any one of the compositions or methods provided herein.

Emulsions are inherently unstable, and emulsifiers are important for both their initial formation and long-term stability. The term "emulsifier" or "emulsifying agent," as used herein, is generally defined as a substance that is capable of lowering the interfacial tension between an oil and an aqueous phase and, thus, aids the dispersal of oil (in the case of oil-in-water emulsions) into droplets of a small size and helps to maintain the particles in a dispersed state. Emulsifiers (or surfactants) are generally classified as amphipathic proteins, lipids, or carbohydrate or synthetic polymers, which act by coating the surface of the dispersed fat or oil particles, thus preventing them from coalescing; such emulsifiers are sometimes also called protective colloids, or long-chain alcohols and fatty acids, which are able to reduce the surface tension at the interface of the suspended particles because of the solubility properties of their molecules. Natural and synthetic emulsifiers (e.g., polysorbates, sucrose esters) can be anionic, cationic, non-ionic and zwitterionic. The zeta potential or charge of the particles can be important in preventing aggregation, coalescence, Oswald ripening, and other phenomenon that destabilize emulsions. All three of the anionic, water-insoluble ascorbyl palmitate, the high HLB anionic saponin, and the anionic *Glycyrrhiza glabra* (licorice) root saponin are anionic and can optimally stabilize particles due to repulsion of negative charges. In addition, the lamellar hydrogel particles formed by ascorbyl palmitate and fibril hydrogel structures formed by *Glycyrrhiza glabra* (licorice) root can further stabilize diverse hydrophobic ingredients, such as those found in complex natural product and pharmaceutical mixture formulations.

"Hydrophile-lipophile balance" or "HLB" refers to the hydrophile-lipophile balance value of a saponin. The HLB may be calculated using the Davies and Riedel method, which considers the chemical structure of a molecule, the HLB value being calculated by integrating the number of each functional group of a molecule with the group unit defined as (HLB=7+$\Sigma$ hydrophilic groups–$\Sigma$ lipophilic groups). The HLB value is on a scale from 0 to 20, with 0 corresponding to a completely hydrophobic (lipophilic) composition, and 20 corresponding to a completely hydrophilic (lipophobic) composition. In one embodiment of any one of the compositions or methods provided herein, the HLB value of the saponin (e.g., anionic) is >10 (e.g., preferably 10-20).

The high HLB saponin (e.g., anionic) may be that of a *Quillaja saponaria* extract (e.g., >13 HLB). Examples of *Quillaja saponaria* extracts include, but are not limited to—Naturale 200V, Uptaia L9, SponovLS, Foamation Q, *Garuda* QUEXT100, *Garuda* QUSAPR70, QL-1000, QL-Ultra, QP-1000, QP UF 300, and other related extracts. *Quillaja* saponin extracts are preferred, in some embodiments, since they are globally approved for use as natural flavoring/emulsifiers in food/beverage and dietary supplements. Alternatively, the high HLB anionic saponin emulsifiers or co-emulsifiers may be derived from natural sources of micellular saponins that include *Yucca* (e.g., Formation Y, BioSol YS-30S, BioSol YS-50LC), tea seeds, bitter melon *Momordica charantia, Panax ginseng*, fenugreek *Trigonella Foenum graecum*, alfalfa root *Medicago sativa*, Siberian ginseng *Eleuthrerococcus senticosus, Astragalus membranaceus, Bacopa monniera, Nigella sativa, Aralia mandshurica, Beyonia alba, Rhaponticum carthamoides, Gymnema sylvestre, Gynostemma pentaphyllum, Withania somnifera, Tinaspora cordifolia*, Milkwort Polygala, *Simlax officinalis*, or *Aesculis hipocastanum*. Any one of the high HLB saponins provided herein can be used as an emulsifier and/or as a co-emulsifier in any one of the compositions provided herein.

In addition, the sweet tasting biosurfactants from *Stevia rebaudiana* (diterpene glycosides-rebaudiosides) and monk fruit mogrosides (Siraitia grosvenorii cucurbitane-type triterpenoid glycosides) may be effective in specific formulations as a co-emulsifier with any one of the high HLB saponins in any one of the compositions or methods provided herein. In addition, natural bacterial rhamnolipid glycolipids biosurfactants and natural hydrocolloid emulsifiers (e.g., gum acacia, beet pectin) may also be used as co-emulsifiers with any one of the high HLB saponins in any one of the compositions or methods provided herein. In applications that do not require a "natural claim", synthetic emulsifiers may also be utilized as co-surfactants.

In an embodiment, the high HLB saponin (e.g., anionic) is also water-soluble at room temperature. As used herein, "water-soluble" refers to the ability of the saponin to be dissolved in water, e.g., at a temperature of 25° C. at concentrations up to 200 PPM (on a dry saponin basis) or 1250 PPM for an extract (e.g., Q-Naturale extract) (e.g., 14% saponins or 14% saponin Q-Naturale liquid extract). The upper limit is based on approved use in the GRAS and Codex approved levels in food/beverage applications. Higher concentrations may be used in pharmaceutical applications. The high HLB saponin (e.g., anionic) (e.g., Q-Naturale liquid extract, ~14% saponins) may be at a concentration of 0.01-1.6 mg/gm in any one of the compositions or methods provided herein.

In an embodiment of any one of the compositions or methods provided herein the *Glycyrrhiza glabra* (licorice) root saponin is a composition with >90% monoammoniumated glycyrrhizinate, ammoniated glycyrrhizin, glycyrrhizic acid, dipotassium glycyrrhizinate, disodium glycyrrhizinate, trisodium glycyrrhizinate, or 18-beta glycyrrhetinic acid or a mixture thereof. The *Glycyrrhiza glabra* (licorice) root saponin may be at a concentration of 0.02-160 mg/gm in any one of the compositions or methods provided herein. The *Glycyrrhiza glabra* (licorice) root saponin can be hot water-soluble. The upper limit is based on approved use limit in food/beverage applications in the USA. Higher concentrations may be used in pharmaceutical applications.

The saponin(s) (e.g., anionic emulsifier or co-emulsifier) may be from any source. The saponin(s) can be in the form of a saponin extract derived from a natural source in any one of the compositions and methods provided herein. The saponin(s) can also be a synthesized molecule in any one of the compositions and methods provided herein. The saponin(s) can be provided in the form of a liquid or powder.

The oil component can be any oil that effectively solubilizes a hydrophobic compound(s). The optimal oil or oil blend used will depend on the chemical properties of the agent(s) or other ingredient(s) or complex formulation(s). Preferably, such oil can also provide a health benefit.

In one embodiment of any one of the compositions or methods provided herein the oil comprises a high oleic acid or medium chain triglyceride.

The oil may be from plants, genetically modified plants, microbial oils, genetically modified microbial oils, marine (e.g., fish) oils, mixtures thereof, etc. Such plants can include algae, flaxseeds, rapeseeds, corn, evening primrose, soy, sunflower, safflower, palm, olive, canola, borage, and mixtures thereof. When such plants are genetically modified, the genetic modifications can include the introduction or modification of polyketide synthase genes. The oil component can also include an oil from a microbial source such as Thraustochytriales, dinoflagellates, and fungal sources.

The oil phase can comprise one or more edible oils. Examples of edible oils include, but are not limited to the following: sunflower oil, coconut oil, vegetable oil, safflower oil, ahiflower oil, corn oil, safflower oil, olive oil, echium oil, flaxseed oil, raspberry seed oil, grape seed oil, borage oil, black currant oil, sea buckthorn fruit oil, sesame seed oil, oat oil, walnut oil, pumpkin seed oil, grapefruit seed oil, moringa and others approved for dietary consumption. In addition, marine oils (e.g., fish, krill, green lipped mussel, etc. that contain DHA/EPA), algal oils (e.g., that contain DHA and/or EPA) and other sources of omega fatty acids may be utilized. Supercritical oil extracts and essential oils approved for oral consumption may also be used (e.g., sage, turmeric, oregano, rosemary), such as to solubilize other hydrophobic agents and/or provide functional activity. In addition, purified fractions of oils may be used including coconut medium chain triglycerides with lauric acid (LCO 100), oleic acid, Neobee (M-5, 1053, 895), Clarinol G-80, Captex (300, 350, 355, 1000, 8000, GTO), Geloil SC, Maisine CC, Gelucire 44/14, Pecol and related carriers. For pharmaceutical or OTC formulations excipients approved as drug excipients (e.g., Labrasol, Labrafil, Gelucire 48/16, Gelucire 44/14) may be used.

Oil ingredients can be used alone or in combination.

The oil phase may also comprise an active agent(s), such as a dietary agent, including nutrient agents, such as vitamins and minerals, and/or pharmaceutical agent(s), which include OTC agent(s), as described in more detail below, and/or other additives or other ingredients. In an embodiment of any one of the compositions or methods provided herein, the oil phase further comprises an herbal compound such as quercetin, ginger, genistein, naringin, sinomenine, piperine, and nitrile glycoside, which improves bioavailability, increases absorption, modifies intestinal permeability, and/or modifies xenobiotic metabolism, etc. In one embodiment of any one of the compositions or methods provided herein, the oil phase further comprises piperine (BIOPERINE®), Triphala, Astragin® or a bile acid.

The water phase may also comprise an active agent, such as a dietary agent, including nutrient agents, such as vitamins and minerals, and/or pharmaceutical agent, as described in more detail below, and/or other additives.

The water phase may, optionally, comprise additional components, such as lactic acid, glycerin humectant, and preservatives. For example, potassium sorbate may be added as a preservative. Natural glycerin replacements can include short-chain fructooligosaccharides that can also act to enhance mineral absorption. Glycerin and/or other humectants may be added to control particle size, solubilize specific active ingredients, inhibit microbial growth, increase viscosity, etc. Exemplary natural humectants include, but are not limited to, glycerin, polysaccharides (e.g., allulose, fructose, glucose, maltose), corn syrup, agave syrup, aloe vera gel/extracts, polyols (e.g. sorbitol, xylitol, mannitol), threhalose, rice syrup (e.g., Moisturlok®), anhydrous betaine, those of mucilaginous plants (e.g., lotus, okra), urea and natural honey. Alternatively, or in addition, polyethylene glycol, propylene glycol, and/or alcohols (e.g. ethanol) may be used for the similar purpose.

The water and/or oil phase of the emulsion may also comprise an antioxidant. The antioxidant(s) can further stabilize the formulation to extend the shelf life due to oxygen, temperature and/or light exposure. The amount of an antioxidant may be in an amount effective to reduce or prevent degradation of an active agent as provided herein, such as, e.g., enzymatic degradation and/or chemical degradation. Non-limiting examples of antioxidant agents include a polyol, a flavonoid, a phytoalexin, an ascorbic acid agent, a tocopherol, a tocotrienol, a lipoic acid, a melatonin, a carotenoid, analogs or derivatives thereof, and combinations thereof. In an embodiment of any one of the compositions or methods provided herein, the antioxidant is a tea polyphenol, rosmarinic acid or a high oxygen radical absorbance capacity (ORAC) compound. Such compounds include antioxidants from goji berries, blueberries, dark chocolate, pecans, artichokes, elderberries, kidney beans, cranberries, etc.

The antioxidant may be water soluble or oil soluble. Oil soluble antioxidants include those of jasmine tea oil, rosemary oil, etc.

The emulsion complexes provided herein can comprise other co-surfactant emulsifiers. Generally, a suitable surfactant/emulsifier for use in an emulsion according to the invention can be a substance which has suitable ecotoxicological properties, i.e., a substance which either in itself or upon degradation is relatively non-toxic. The emulsifier or co-emulsifier of emulsions of the present invention can include any emulsifier (e.g., non-ionic, cationic or anionic), including polysorbate esters, lecithin, monoglycerides, diglycerides, organic acid esters of monoglycerides, propylene glycol esters of fatty acids, polyglycerol esters of fatty acids, propylene glycol monostearate, sorbitan monostearate, sorbitan trioleate, and sodium lauryl sulfate.

The emulsion complexes of the invention may further include surfactants such as ascorbyl-6 palmitate; stearylamine; pegylated phospholipids, sucrose fatty acid esters and various vitamin E derivatives comprising α-tocopherol nicotinate, tocopherol phosphate, and nonionic, synthetic surfactant mixtures, such as polyoxypropylene-polyoxyethylene glycol nonionic block copolymer (e.g., TPGS).

The emulsion complexes of the invention may further include a stabilizing hydrophilic agent. Such agents include cyclodextrin, maltodextrin (or other starch), beta glucan (e.g., cereal (e.g., oat), yeast, mushroom, etc.), dietary fiber (e.g., galactomannan, guar gum, acacia gum), natural emulsifier protein (e.g., pea, soy, whey, potato, casein), cationic carrier (e.g., poly-l-lysine, chitosan shellfish, chitosan mushroom), or a combination thereof.

The emulsion complexes of the invention may further include a viscosity modifier, such as a humectant or mucilaginous ingredient (e.g., glycerin, allulose, Moisturlok® (e.g., rice syrup and grape extract), Honey, Agave Syrup, Aloe Vera extracts, trehalose, sucrose, betaine, glycerol, glucose syrup, polyethylene glycol, sugar alcohols (e.g., maltitol, sorbitol, xylitol, isomaltulose), dietary fibers, fructooligosaccharides (FOS), galactooligosaccharides (GOS), chicory extracts, Jerusalem artichoke extracts, optunia cactus extract, lotus seed extract, fenugreek fibers, seaweed extracts, and related compounds). Such modifiers may have varying levels of sweetness.

The emulsion complexes provided herein may provide pH-sensitive release: that is, they are stable at specific pH levels (e.g., low, such as gastric pH) and release agent(s) at other pH levels (e.g., the neutral pH of the small intestine). As used herein, "pH-sensitive release" refers to a rate of release that is dependent on or regulated by the pH of the surrounding media or environment of the delivery system. Certain embodiments of the delivery systems provided herein are stable in a gastric acid environment (e.g., pH 1.5-3.5), but capable of releasing their loads (e.g., nutrients, pharmaceuticals) at the neutral pH levels (and high salt concentration) of the small intestine.

The emulsion complexes provided herein can be thixotropic. Thixotropic fluids are characterized by a viscosity which not only varies substantially with changing shear rate, but which also varies with time at a given rate. The viscosity of a thixotropic fluid decreases from a relatively high initial value as shear rate increases to a substantially lower value. Then as the shear rate decreases, viscosity slowly increases again, rebuilding to a value which is still less than the original high initial value. That is, as the shear rate is decreased, the recovery in viscosity is incomplete. Compared to the unsheared material, a lower viscosity for any given shear rate initially results. However, this loss in viscosity at any given shear rate is temporary and time-dependent. In a truly thixotropic material, given sufficient time, the viscosity will completely rebuild to its original non-sheared value. Thixotropic properties of a substance can be determined visually but also may be measured using a thixotropic index, a ratio of the material's viscosity at two different speeds, which are typically different by a factor of 10 (e.g., the ratio of the apparent viscosity at 10 RPM to the apparent viscosity at 100 RPM).

The emulsion complexes provided herein can also exhibit a glass-transition temperature of between 50-80° C. Generally, above glass-transition temperatures the emulsion complex is clear and when temperature decreases below 55° C. the ingredients become white with visible particles that sediment upon prolonged storage for a few hours. Glass-transition is the phenomenon in which a solid amorphous phase gradually and reversibly transitions from a hard "glassy" state into a viscous or rubbery state as temperature increases. Glass-transition is the phenomenon in which a solid amorphous phase gradually and reversibly transitions from a hard "glassy" state into a viscous or rubbery state as temperature increases. Further, the *Glycyrrhiza glabra* (licorice) root can form a fibrillar hydrogel when cooled to room temperature. Thus, for effective loading of the oil into an emulsion system as provided herein, the temperature of emulsification needs to be higher than the glass-transition temperature. This is an embodiment of any one of the methods provided herein.

Other aspects of the present invention include a method for forming an emulsion complex. The method includes combining an oil mixture and water mixture and other components as provided herein. The various components of the emulsion can be combined with moderate to high shear mixing. Use of ultra high shear homogenizers (e.g., microfluidizer) is not required to create the emulsion complexes provided herein. As used herein, "high shear mixing" refers to >4000 RPM using inline or overhead shaft Silverson mixer (or similar units (e.g., equivalent inline or overhead mixers), such as by Ross or IKEA) with a general purpose or emulsor head. As used herein, "low shear mixing refers to using a low shear propeller or low speed Silverson mixer. Generally, the RPMs at low shear are about 2500. Also Likiwifer or similar low shear mixers can be used to hydrate ingredients in large batches. In lab Silverson LM5-A tubular mixer (with various shear heads) can be used to develop protocols for commercial production.

In one embodiment, the water phase is synthesized as follows. The glycerin (or ALLSWEET® allulose) and lactic acid are added to double-distilled water (ddH$_2$O) at room temperature. The mixture is then heated to 75° C. and low shear (e.g., 2500 RPM) mixing occurs while the remaining ingredients (Cytoguard OX-OST, potassium sorbate, Q-Naturale 200V, Glycyrrhizin monoammoniated MM100F, and ascorbyl palmitate) are added sequentially. Each ingredient is added only after the previous ingredient has been completely dissolved into the water phase.

In an embodiment of any one of the methods provided herein, the pH of the water phase is maintained to be between pH 3-5 and/or with a temperature that is greater than 55° C. (e.g., greater than 55° C. and less than 95° C.). It has been found that at a temperature of less than 55° C. the solution can be opaque with visible white glass-like particles.

To add vitamins, minerals, and/or other additives, the edible oil is heated to 65° C. at a low shear (e.g., 2500 RPM) and protected from light, and each vitamin, mineral, or additive can be added sequentially to the mixture. As one example, CytoGuard OX-OST (oil soluble tea extract), d-alpha tocopheryl acetate in sunflower oil, beta-carotene in sunflower oil, vitamin D3 (as cholecalciferol) in medium chain triglycerides (MCTs), vitamin A (as retinyl palmitate), vitamin K1 oil, vitamin K2-7 (on maltodextrin), and BIO-PERINE® are added. The oil phase may be mixed at a low shear (e.g., 2500 RPM) and maintained at 65° C. while protected from light until it is ready to be added to the water phase.

To create the O/W emulsion complex, the oil phase can be slowly added into the water phase at 75° C. with high shear (e.g., 5000 RPM).

Oil soluble agents or other ingredients can be provided or in the form of an oil, powder, or complexed to water-soluble carrier (e.g., maltodextrin, guar gum).

In emulsion complexes, water is typically present in an amount from about 10 wt. % to about 90 wt. %, more preferably from about 20 wt. % to about 80 wt. %, and even more preferably from about 50 wt. % to about 70 wt. %. Emulsion complexes of the present disclosure are highly stable in terms of both physical stability (i.e., lack of separation of components) and chemical stability (i.e., lack of oxidation of the oil component). Physical stability can be measured in a variety of ways. Simple visual observation of physical separation or "creaming" is an indication of separation. Another measure of physical stability is a lack of change in the particle size of micron particles formed in the emulsion. As emulsions separate, the size of particles becomes greater. In preferred embodiments of the invention, the particle size will not increase more than about 15%, more preferably not more than about 25%, more preferably not more than about 30%, more preferably not more than about 40%, and more preferably not more than about 50%, after storage at 42° C. within 30 days, within 90 days, and within 180 days.

The emulsion complexes described herein exhibit unique feature(s) during cooling from 60° C. to room temperature, such as resulting in phase separation of some ingredients that rapidly reverses to stable hydrogel upon inversion and/or gentle mixing at room temperature. Any one of the emulsion complexes provided herein can have such feature(s).

Chemical stability of an emulsion complex can be measured in terms of oxidation of any of the species of the oil component. Oxidation can be measured by the production of secondary products of oxidation, such as by measuring peroxide values, anisidine values, or alkenal values or by conducting a headspace analysis.

In some embodiments, the emulsion complexes have a particle size (mean droplet diameter) of 100 to 900 nm, for example, 100 to 200 nm, or 100 to 500 nm. Droplet size can be verified by using particle sizing instruments, such as the commercial Sub-Micron Particle Analyzers (LumiSizer, LISST, Nanosizer), and the parameters can be varied until substantially all droplets fall within the preferred diameter range. Both dynamic light scattering and laser diffraction instruments were used to study emulsion complexes and hydrogels comprising pectin provided herein. By "substantially all," it is meant at least 80% (by number), preferably at least 90%, more preferably at least 95%, and most preferably at least 98%. The particle size distribution is typically Gaussian, so that the average diameter is smaller than the stated limits.

Another example of a preferable delivery matrix is a fluid gel delivery matrix where an emulsion is complexed with a cation such that a low viscosity sheared fluid gel (e.g., micron particle) results. Such fluid gels can be stable at low pH (e.g., gastric pH) and release agents(s) at neutral pH levels (e.g., in the small intestine).

Fluid Gel Delivery Matrix

"Fluid gel delivery matrix" (sheared gel) refers to a suspension of micro-gelled particles (e.g., micron particles) dispersed in an aqueous solution, and, therefore, exhibits some level of viscosity as well as the ability for suspension. The O/W emulsion complex is generally encapsulated within the sheared fluid gel microparticles and can deliver ingredients to specific areas of the digestive tract. Typically, fluid gels are pourable fluid masses with very short micron-sized beads creating flowable textures (e.g., similar to pulp in orange juice or finer small particles that are not visible to the naked eye). Different textures and flow properties can be obtained by modifying the concentration of certain ingredients, temperature, shear rate, and ion types and levels. If desired, in an embodiment of any one of the methods provided herein, the pectin gel does not have to be sheared (and is not so sheared) to create other solid formulations with the consistency of Jell-O™ or yogurt.

In one aspect, an O/W emulsion complex can be complexed with a low ester pectin in the presence of cations, such as specific divalent cations to form a fluid gel. It has been found that the O/W emulsion complex can be effectively and homogeneously complexed with the low ester pectin (e.g., nearly 100%) in some embodiments (e.g., with an anionic low ester amidated pectin in the presence of specific divalent cations). "Low ester pectin", as provided herein, refers to pectins with 10-40% ester groups. Preferably, the low ester pectin is a citrus peel or apple pectin. They may have high, medium or low calcium sensitivity. Importantly, it was found that high ester (>60%) citrus peel and apple pectins not sensitive to divalent cation gelation did not induce binding of emulsion to the pectin to create a sheared fluid gel.

The pectins may be amidated. In amidated pectins, the methyl esters are replaced with amide groups. The molecules also comprise regions of neutral sugars (e.g., arabinose, galactose, rhamnose). The pectins may be extracted, for example, from citrus peel (e.g., lemon peel), apple pomace, or other sources. Pectin may be produced by any method known in the art, for example, by extraction of citrus rind in hot, acidified water followed by isolation from the ensuing solution. The pectins provided herein may be from any source. In some embodiments, the pectin molecule is synthesized.

The low ester pectin may be in a concentration of 1-10 mg/gm in any one of the delivery matrices provided herein.

Exemplary cations include divalent cations. Divalent cations include, but are not limited to, calcium and zinc. Many forms of calcium and zinc conjugates were found to induce gelation (e.g., citrates, glycinates, gluconates, lactates, maleates, aspartates, phosphates). Other divalent cations include, magnesium, manganese, cobalt, and ferrous iron, although magnesium and manganese were less effective at gelation. Other cationic natural preservatives that can also induce gelation and/or complex with anionic particles in specific formulations include, but are not limited to, poly-L-lysine, lauric arginate, and chitosan.

Methods of synthesizing fluid gels are known in the art. It is an important part of the process that the gel is subjected to shear as it cools through the gelation temperature. By subjecting to shear is to be understood subjecting to any suitable form of agitation which results in a fluid gel. For example, the solution may be sheared, stirred, shaken, disrupted, homogenized or agitated in any other way such as using ultrasound. Shearing may be conducted at a constant rate, i.e., controlled shearing, for instance in a rheometer. Shearing may also be conducted at a non-constant rate, i.e., non-controlled shearing, for instance with a mechanical stirrer. Any suitable rate of shearing may be used.

Typically, the shearing takes place while the solution cools from above the gelation temperature of the mixture, typically to room temperature. Normally the cooling takes place naturally, that is the gel cools gradually to room temperature. However, either natural cooling or quench cooling may be used. Any manner of cooling which results in a fluid gel may be used. The solution may also be alternately quench cooled (e.g., with ddH$_2$O) and naturally cooled when appropriate. Water jacketed tanks and other process methods can be used to precisely and rapidly cool large volumes of fluids.

The shearing and cooling are typically simultaneous. Shearing may be conducted throughout the entire cooling process, or only during cooling through the gelation temperature. Shearing and cooling may take place contemporaneously or sequentially, for instance, as alternating steps. For example, the solution may be sheared while being held at a constant temperature and then allowed to cool, followed by further shearing at a lower constant temperature and subsequent cooling. However, it is important that shearing takes place as the solution gels, that is as the solution cools through the gelation temperature.

The viscosity of the resulting gel can be partly dependent on the temperature to which the starting solution is heated prior to cooling and shearing. For instance, the viscosity of a gel which results from heating the starting solution to 90° C. is generally higher than the viscosity of a corresponding gel which results from heating the starting solution to 70° C. or 50° C. The properties of a gel of the invention may thus be changed by appropriate modification of the temperature to which the starting solution is heated. However, other factors such as the addition of electrolyte can also affect the properties of the gel.

In a particular embodiment, the gel is synthesized from any one of the O/W emulsion complexes described herein. Prior to adding a low ester pectin to the O/W emulsion complex, the low ester pectin is mixed at room temperature with moderate shear with ddH$_2$O. The mixture is then heated to 80° C. to hydrate the pectin. After hydration, the mixture is cooled to room temperature and slowly added to the O/W emulsion with high shear. Other methods to effectively hydrate pectin, such as glycerin, may be used in some formulations.

After the pectin has been added, the resulting mixture is cooled to 42° C. at low shear, and additional vitamins, minerals, herbal extracts, and other additives may be incorporated sequentially into the fluid gel delivery matrix. The addition of one or more cations (e.g., divalent cations) during this phase can facilitate very efficient (>90%) and homogeneous complexation between the O/W emulsion complex and the fluid gel delivery matrix.

Further, in some embodiments, at least one acidulant is added. Acidulants are used to lower the pH of the composition. Examples of acidulants include, but are not limited to, lactic acid, phosphoric acid, fumaric acid, sulfuric acid, adipic acid, tartaric acid, succinic acid, acetic acid, propionic acid, citric acid, malic acid, or combinations thereof. In some embodiments, the acidulant is lactic acid. In some embodiments, however, the acidulant that is added does not cause the formation of insoluble complexes with the cations (e.g., divalent cations). In some embodiments, citrates are not used. In other embodiments, citrates are added.

Also, Likiwifer or similar low shear mixers can be used to hydrate ingredients in large batches.

The zeta potential of particles in the O/W emulsions (e.g., hydrogels) provided herein can be tested for each combination to ensure efficient and homogenous binding to pectin. In an embodiment of any one of the methods provided herein, such a step is included in the method. In an embodiment of any one of the compositions provided herein, the net charge of O/W emulsion particles (e.g., hydrogel) (e.g., zeta potential) is negative at pH 3 to 5.

In an embodiment of any one of the compositions or methods provided herein, when pectin is included the composition further comprises or the method further comprises adding an emulsifier and/or co-emulsifier that is not nonionic (e.g., anionic).

In another aspect, it has also been found that fluid gel delivery systems or O/W emulsion complexes can be modified to form a viscous hydrogel delivery matrix with a beta glucan and one or more other components. It was found that oat beta glucan can form a viscous hydrogel at lower temperatures that will not melt pectin microbeads. At temperatures below 45° C. addition of acacia gum and/or a fructooliogsaccharide (FOS) and/or galactooligosaccharide (GOS) and/or a hydrocolloid (e.g., high methoxy pectin, gellan gum) may be included in specific formulations to inhibit syneresis, improve texture, mouth feel, and/or to promote gut health (e.g., microbiome, intestinal permeability). The hydrogel delivery matrix described herein need not require the use of typical hydrocolloid thickeners (e.g., Xanthan gum, guar gum, konjac) that are known to inhibit nutrient absorption/bioavailability. Thus, in an embodiment of any one of the hydrogel delivery matrices provided herein can comprise beta glucan, and any one or more of (1) acacia gum, a fructooliogsaccharide (FOS), a galactooligosaccharide (GOS), and a hydrocolloid. In an embodiment, beta glucan, and any one or more of acacia gum, a fructooligsaccharide (FOS), a galactooligosaccharide (GOS), and a hydrocolloid are added sequentially to the fluid gel delivery system mixture under the same conditions (e.g., 42° C. at low shear).

In an embodiment of any one of such methods, other pH, salt, or gastrointestinal enzyme or cation responsive hydrocolloid (e.g., alginate, gellan, carrageenan) are also added (e.g., sequentially). Combinations of divalent ion sensitive hydrocolloids (e.g., gellan gum, alginate, carrageenan), cationic chitosan (e.g., shellfish and mushroom), digestible or non-digestible hydrocolloids (e.g., locust bean gum), gel forming natural products (e.g. chondroitin, glucosamine, hyaluronate, fucoidan), etc. can be added.

The hydrogels delivery matrices provided herein can be used to improve the bioavailability of hydrocolloid(s) (e.g., natural hydrocolloids) that are mucoadhesive (e.g., myrrh, khaya, alginate) and mucolytic compounds (e.g., natural mycolytic compounds (e.g., n-acetylcysteine) in some embodiments. Thus, in any one of the compositions or methods provided herein such hydrocolloid(s) and/or mucolytic compound(s) are included.

Hydrogel Delivery Matrix

"Hydrogel delivery matrix" refers to a three-dimensional hydrophilic material possessing the ability to swell in water and to retain a significant portion of water within its structure without dissolving. A "biodegradable hydrogel" is a hydrogel system comprising at least one biodegradable component (e.g., a component which is degraded by water and/or enzymes found in nature).

The hydrogels can be formed with beta glucans, which are glucans with a β(1→3)-linked glucopyranosyl backbone, or a β(1→4)-linked glucopyranosyl backbone, or a mixed β(1→3)(1→4)linked glucopyranosyl backbone. Beta glucans are naturally-occurring constituents of cell walls in essentially all living systems including plants, yeast, bacteria, and mammalian systems. Its effects and modulating actions on living systems have been studied extensively (see Abel, G., and Czop, J. K., "Stimulation of Human Monocyte B-Glucan Receptors by Glucan Particles Induces Production of TNF-∂ and 1L-B", Int. J. Immunopharmacol., 14(8): 1363-1373, 1992 and references included therein). Beta glucans, when administered in experimental studies, can elicit and augment host defense mechanisms including the steps required to promote healing by first intent, thereby stimulating the reparative processes in the host system. Beta glucans can be rapidly removed from tissue sites through macrophagic phagocytosis or by enzymatic destruction by serous enzymes. Beta glucans can be effective in hydrogels due to their rapid destruction or removal, as well as their available viscosity and lubricous nature. Further, beta glucans are known to improve bioavailability by increasing lymphatic absorption to reduce first pass liver metabolism.

In some embodiments, the beta glucan is a cereal beta glucan. Examples of such beta glucans include, but are not limited to, the following: oat (e.g. Nutrim®, Oatwell®, PromOat®, SweOat®), barley, wheat, rye, and combinations thereof. Other examples of beta glucan include, but are not limited to those of yeast (e.g., Polycan®, Wellmune®, BGF-Immune®, Yestium®), algae (e.g., Euglena®, Betavia®, Paramylon, Algamunee®), mushroom (e.g., AHCC® lentinula edodes, Maitake), etc. In any one of the compositions or methods provided herein the beta glucan is in a concentration of 2-30 mg/gm.

The hydrogels are also further stabilized from syneresis in some embodiments. With acacia gum, high methoxy pectin, or a variety of viscosity modifying agents at temperatures lower than 45° C. to prevent melting of pectin microparticles. In any one of the compositions or methods provided herein the acacia gum is in a concentration of 1-50 mg/gm, such as 2-30 mg/gm.

The beta glucans and/or other components of the hydrogels can be from any source. They can be derived from naturally occurring substances or can be synthesized.

Aqueous solutions, suspensions, fluids, or gels comprising beta glucan and other components can be produced that have favorable physical characteristics as a hydrogel. The viscosity can vary from a thin liquid to a firm, self-supporting gel.

The hydrogels (e.g., viscous hydrogels) can also be formed with other divalent ion sensitive gelation hydrocolloids (e.g., gellan gum, alginate, carrageenan), locust bean gum, proteins (e.g., pea, potato, milk, soy), fiber (e.g., larch arabinogalactan, flax seed, fenugreek, psyllium, inulin), mucilaginous extracts (e.g., lotus, okra, Mucosave®, Opunxia®), cold set starches, cyclodextrin (e.g., alpha, beta and gamma), gel-forming natural products (e.g., glucosamine, hyaluronate, fucoidan), etc.

The hydrogels can also include other soluble fiber ingredients (e.g., FOS or GOS) that increase nutrient and mineral absorption. Such ingredients can be at a concentration of 1-100 mg/gm in any one of the compositions or methods provided herein.

Molecules that reduce syneresis and increase viscosity include, but are not limited to, cold set plant extracts (e.g., Pregeflo®, Glucidex®, Perfectasol®, Solanic®, Risolubles®), dietary fibers (e.g., larch arabinogalactan, flax seed, fenugreek, psyllium, inulin, Sunfiber®, Orafti®, Oliggo®), proteins (e.g., pea, potato, milk, soy), cyclodextrin (e.g, alpha, beta and gamma), beet pectin and high methoxy calcium insensitive pectins, etc.

Gut healthy fibers that improve nutrient bioavailability, target ingredients to specific areas of gastrointestinal tract, and/or promote healthy microbiome include, but are not limited to mucilaginous extracts (e.g., Aloe vera, lotus, okra, Mucosave®, Opunxia®), Astragin® extract, and specific hydrocolloids and dietary fibers that have distinct digestion profiles in different segments of the digestive system. Such ingredients ca also bind specific receptors to enhance absorption in specific areas of the digestive system. For example, chitosan and related cationic complexes deliver ingredients to the stomach. Non-digestible calcium insensitive hydrocolloids can delay small intestine absorption and target ingredients to the large intestine.

To complete synthesis of a hydrogel delivery system, the mixture can be cooled to room temperature, the final ingredients (e.g., temperature-sensitive ingredients) are added (for example, flavoring(s), vitamins, etc.), and the weight of the mixture is adjusted using ddH$_2$O. The resulting hydrogel can be nitrogen-purged to displace oxygen to reduce oxidation prior to sealing/storage.

In some embodiments, any one of the delivery matrices provided herein further comprises a flavoring agent (e.g, a bioactive flavoring agent), such as beta-caryophyllene, vanillin, linalool, etc. The flavoring may be a natural flavor with a variety of taste masking agents to increase palatability of the formula and can be incorporated into oil phase or water phase depending on their solubility.

In lab Silverson LM5-A tubular mixer (with various shear heads) can be used to develop protocols for commercial production.

The fluid gels and hydrogels described herein typically are viscous, having viscosities in the range of 10,000-100,000 cps. For example, any one of the gels provided herein can have a viscosity of 50,000-50,000 cps. Viscosity is a measurement of a fluid's resistance to deformation at a given rate, that is, the frictional force that arises between adjacent layers of fluid that are in relative motion to one another. Methods of measuring viscosity are well known in the art and include, for example, using viscometer (e.g., falling ball viscometers, glass capillary viscometers, tuning fork vibration viscometers, and rotational viscometers), viscosity cups, consistometers, or rheometers.

The delivery systems provided herein are, generally, stable at low pH levels (e.g., gastric pH levels), such as 1, 2, 3, or 4 (e.g., 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 3.1, 3.2, 3.3, 3.4, 3.5, 3.6, 3.7, 3.8, 3.9, 4.0, or 0-1, 0-2, 0-3, 0-4, 1-2, 1-3, 1-4, 1,5-2, 1.5-2.5, 1.5-3, 1.5-3.5, 1.5-4, 2-2.5, 2-3, 2-3.5, 2-4, 2.5-3, 2.5-3.5, 2,5-4, 3-4, 3.5-4), but agent(s) release and digestion occurs at higher pH levels (e.g., neutral pH levels of the small intestine), such as 6, 7, or 8 (e.g., 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 6-7, 6.5-7, 6.5-7.5, 7-8, 7.5-8).

Measurement of the pH-sensitive release can be performed using any method know in the art. As a non-limiting example, drug release can be determined using in vitro studies. A given formulation may be incubated with a dissolution medium (e.g., a solution having a pH greater than 3.5, for example, PBS) and then agitated. For example, USP simulated gastric fluid, USP simulated intestinal fluid, Fed State Simulated Intestinal Fluid (FeSSIF-V2), Fasted State Simulated Intestinal Fluid (FaSSIF), and/or Fasted State Simulated Gastric Fluid (FaSSGF) may be used, such as in USP 771-approved dissolution methods. Samples are then withdrawn at specified time points, for example 5, 10, 15, 20, 25, 30, 40, 50, 60 minutes, 2, 4, 6, 8, 10 and 24 hours. The samples are then filtered, diluted with mobile phase, and quantified using HPLC or with a UV-Vis spectrophotometer (using a previously determined standard curve). Release kinetics may be determined using the following equation:

$$kt^n = \frac{M_t}{M\infty}$$

Where M is the amount of drug released at time t, k is the release constant, Moo is the total amount of drug released, and n is the release exponent. The value of n determines the relationship between rate and time.

Chewable Gum or Gummies

Resulting hydrogels (e.g., viscous hydrogels), in some embodiments, maybe further processed to form chewable gum or gummies. "Gummies" dissolve when chewed and do not require additional ingredients. "Chewable gum" or "chewing gum" or the like refers to a water insoluble gum base, a water soluble portion, and, optionally, flavors. The water soluble portion dissipates with a portion of the flavor over a period of time during chewing. The gum base portion is retained in the mouth throughout the chew. The insoluble gum base generally comprises elastomers, resins, fats and oils, softeners, and inorganic fillers. The gum base may or may not include wax. The insoluble gum base can constitute approximately 5 to about 95 percent, by weight, of the chewing gum, more commonly, the gum base comprises 10 to about 50 percent of the gum, and in some preferred embodiments, 20 to about 35 percent, by weight, of the chewing gum. As described herein, the chewing gum may be any of a variety of different chewing gums including low or high moisture, sugar or sugarless, wax-containing or wax-free, low calorie (via high base or low-calorie bulking agents), and/or may contain other dental health agents.

Thus, chewable gum or gummies may be used to administer various dental pharmaceutical agents, as well as for the controlled release of other agents, e.g., dietary agents, nutrient agents, flavoring agents, etc. Pharmaceutical applications of pharmaceutical chewing gums or gummies include topical treatment of oral diseases and systemic delivery after absorption through the buccal mucosa or the gastrointestinal route. Chewable gum or gummies have several benefits, including: consumption without water, high acceptance by children, low side effects, suitable stability, high bioavailability, rapid onset effect, and relieving the mouth dryness by stimulating saliva. Factors affecting drug release in this type of dosage form include physicochemical properties of the active ingredient, chewing gum or gummy properties, and related factors with strength and number of masticatory movements.

In some embodiments, the chewable gum or gummies comprises active ingredients (e.g., nutrients, pharmaceuticals), gum bases, fillers, elastomers, plasticizers, softeners, emulsifiers, sweeteners and flavors. Examples of formulated drugs in the form of chewing gum or gummies can include fluoride, chlorhexidine, nicotine, aspirin, caffeine, and dimenhydrinate. Others are also possible, as described herein.

Synthesis of the chewable gum or gummies, in some embodiments, results from dehydration of a hydrogel described above. By removing 25-75% of the water from the gel, the resulting compound may be reformulated into chewable gum or gummy. The gel may be dehydrated into chewable gum or gummies by any method known in the art, for example, with heat, or lyophilization. Alternatively, agar, starch, pectin, cellulose gum, locust bean gum, and related natural hydrocolloids may be utilized increase viscosity for gum and gummy formulations.

Powder

In still further aspects of the disclosure, powders are provided. The powders, in some embodiments, may be prepared by removing water from any of the delivery matrices provided herein. The water may be removed, for example, by spray drying, lyophilization, or any method known in the art. Carriers such as maltodextrin, guar gum, etc. may be used. Additional pharmaceutical approved carrier excipients can be used for specific formulations.

"Powder" refers to a collection of essentially dry particles, i.e. the moisture content being below about 10% by weight, preferably below 6% by weight, and most preferably below 4% by weight. The particles that make up the powder can be characterized on the basis of a number of parameters including, but not limited to, average particle size, average particle density, particle morphology (e.g., particle aerodynamic shape and particle surface characteristics) and particle penetration energy (P.E.).

The average particle size of the powders according to the present invention can vary widely and is generally from 0.1 to 250 m, for example from 10 to 100 m and more typically from 20 to 70 m. The average particle size of the powder can be measured as a mass mean aerodynamic diameter (MMAD) using conventional techniques such as microscopic techniques (where particles are sized directly and individually rather than grouped statistically), absorption of gases, permeability or time of flight. If desired, automatic particle-size counters can be used (e.g., Aerosizer Counter, Coulter Counter, HIAC Counter, or Gelman Automatic Particle Counter) to ascertain the average particle size. Actual particle density or "absolute density" can be readily ascertained using known quantification techniques such as helium pycnometry and the like. Alternatively, envelope ("tap") density measurements can be used to assess the density of a powder according to the invention. The envelope density of a powder of the invention is generally from 0.1 to 25 $g/cm^3$, preferably from 0.8 to 1.5 $g/cm^3$. Envelope density information is used to characterize the density of objects of irregular size and shape. Envelope density is the mass of an object divided by its volume, where the volume includes that of its pores and small cavities but excludes interstitial space. A number of methods of determining envelope density are known in the art, including wax immersion, mercury displacement, water absorption and apparent specific gravity techniques. A number of suitable devices are also available for determining envelope density, for example, the GeoPyc™ Model 1360, available from the Micromeritics Instrument Corp. The difference between the absolute density and envelope density of a sample composition provides information about the sample's percentage total porosity and specific pore volume.

Particle morphology, particularly the aerodynamic shape of a particle, can be readily assessed using standard light microscopy. It is preferred that the particles which make up the instant powders have a substantially spherical or at least substantially elliptical aerodynamic shape. It is also preferred that the particles have an axis ratio of 3 or less to avoid the presence of rod- or needle-shaped particles. These same microscopic techniques can also be used to assess the particle surface characteristics, e.g. the amount and extent of surface voids or degree of porosity.

Particle penetration energies can be ascertained using a number of conventional techniques, for example a metallized film P.E. test. A metallized film material (e.g., a 125 μm polyester film having a 350 Å layer of aluminum deposited on a single side) is used as a substrate into which the powder is fired from a needleless syringe (e.g., the needleless syringe described in U.S. Pat. No. 5,630,796 to Bellhouse et al) at an initial velocity of about 100 to 3000 m/sec. The metallized film is placed, with the metal coated side facing upwards, on a suitable surface. A needleless syringe loaded with a powder is placed with its spacer contacting the film, and then fired. Residual powder is removed from the metallized film surface using a suitable solvent. Penetration energy is then assessed using a BioRad Model GS-700 imaging densitometer to scan the metallized film, and a personal computer with a SCSI interface and loaded with MultiAnalyst software (BioRad) and Matlab software (Release 5.1, The MathWorks, Inc.) is used to assess the densitometer reading. A program is used to process the densitometer scans made using either the transmittance or reflectance method of the densitometer.

Agents and Uses

The delivery systems described herein can be configured to deliver liquid, semi-liquid, or solid forms of agents. In some embodiments, the delivery system comprises more than one agent, such as 2, 3, 4, 5, 6, 7, 8, 9, 10 or more different agents. The agents can be dietary agents, such as nutrient agents, or pharmaceutical agents, such as over-the-counter (OTC) drugs. The agents can be for any subject, including human or other animal subjects, such as pets. "Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

The agents include dietary agents which include, but are not limited to, all known natural products (~300,000 see dnp.chemnetbase.com/faces/chemical/Chemical-Search.xhtml), US approved GRAS (generally regarded as safe), Herbs of Commerce, FDA filed new dietary ingredients (NDA), biologics (e.g., enzymes, probiotics, lactoferrin), and agents from the Traditional Chinese Medicine database, etc. Agents may be from any source, such as any natural source or synthetic bioequivalents. Agents may be native or extracted (e.g., water, ethanol, supercritical) and may include synthetic versions and/or cell culture-derived ingredients. Such agents include functional food and beverage agents, dietary supplements as well as nutrient agents. Nutrient agents include vitamins and minerals. Vitamins and minerals include, but are not limited to, the following: calcium, L-carnitine, choline, chromium, copper, fluoride, folic acid, inositol, iodine, iron, magnesium, manganese, molybdenum, phosphorus, potassium, selenium, sodium, sulfur, taurine, zinc, vitamin A, vitamin B1 (thiamin), vitamin B2 (riboflavin), vitamin B3 (niacin), vitamin B5 (pantothenic acid), vitamin B6 (pyridoxine), vitamin B6, vitamin B7 (biotin), vitamin B9 (folate), vitamin B12 (cobalamin), vitamin C, vitamin D, vitamin E, and vitamin K. Other nutrients include proteins, carbohydrates, lipids, probiotics, micronutrients, and combinations thereof.

In one embodiment, a delivery matrix described herein comprises one or more vitamins selected from the group consisting of thiamin, riboflavin, pyridoxine, niacin, pantothenic acid and/or pantothenate, folic acid, biotin, vitamin B12, vitamin A, vitamin E, one or more tocopherols, vitamin D3 or cholecalciferol, vitamin K. In one embodiment, the pantothenate is calcium pantothenate. In another embodiment, the tocopherol is DL-alpha tocopheryl acetate. In another embodiment, vitamin K is an MSB complex.

In one embodiment, the delivery matrices described herein further relate to a medical food comprising macronutrients and micronutrients. Exemplary macronutrients include, but are not limited to proteins, sugars, and fats. In one embodiment, the macronutrients are selected from the group consisting of casein, sucrose, corn starch, and corn oil. The casein, in some embodiments, is low Cu and Fe casein. Casein refers generally to one or more related phosphoproteins commonly found in mammalian milk. Corn oil is a complex mixture comprising various amounts of saturated fatty acids, monounsaturated fatty acids, and polyunsaturated fatty acids. In one embodiment, the medical food of the invention includes all the vitamins recited herein. Animal (e.g., whey isolates), insect, mushroom and plant (e.g., pea, potato, hemp) can be used for sources of protein, fat and carbohydrates with various functional activities and incorporated in the delivery matrices provided herein.

In one embodiment, the delivery matrices described herein further comprises one or more elements, ions, or minerals, selected from the group consisting of calcium, phosphorus, potassium, sodium, chlorine, magnesium, copper, iron, zinc, manganese, iodine, selenium and trace mineral extracts, such as shilajit, marine, fulvic acid or soil-derived. In one embodiment, the iron is present as ferric citrate. In one embodiment, the delivery matrix comprises little to no iron. In another embodiment, the delivery matrix of the invention has added iron. In one embodiment, the delivery matrix includes all the elements, ions, or minerals recited herein, except iron. In one embodiment, the delivery matrix includes all the elements, ions, or minerals recited herein. Ingredients may be encapsulated in the delivery matrices to prevent reactions between them, improve the taste profile, etc.

In another embodiment, the delivery matrices described herein further comprise an amino acid. In one embodiment, the amino acid is selected from the group consisting of histidine, alanine, isoleucine, arginine, leucine, asparagine, lysine, aspartic acid, methionine, cysteine, phenylalanine, glutamic acid, threonine, glutamine, tryptophan, glycine, valine, pyrrolysine, proline, selenocysteine, serine, and tyrosine. In one embodiment, the amino acid is methionine. In one embodiment, the amino acid is DL-methionine.

In another embodiment, the delivery matrix comprises choline. In one embodiment, choline is present as choline bitartrate. Other forms include glycerol phosphoryl choline, lecithin (soy, sunflower), etc.

Agents also include pharmaceutical agents. Pharmaceutical agents include drugs or other medicines that have a pharmacological property. Pharmaceutical agents include over-the-counter (OTC) medications.

Pharmaceutical agents include, for example: analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-parkinsonian agents, gastro-intestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents anti-obesity agents, cognition enhancers, anti-urinary incontinence agents, nutritional oils, anti-benign prostate hypertrophy agents, essential fatty acids, non-essential fatty acids, and mixtures thereof. Ant-inflammatory agents, include nonsteroidal and steroidal anti-inflammatory agents, such as indomethacin, diclofenac, flurbiprofen, aspirin, dexamethasone, budesonide, beclomethasone, flucticasone, tioxocortal, and hydrocortisone; immunosuppressants, such as cyclosporin; anti-anginals and anti-hypertensives; anti-spasmodics; anti-colitis drugs, such as 5-aminosalicylic; and anti-arrhythmia agents, such as quinidine, verapamil, procainamide and lidocaine; protein or peptide drugs, such as insulin, human growth hormone, interleukin-II, interferon, calcitonin, leuprolide, tumor necrosis factor, bone growth factor, melanocyte-stimulating hormone, captopril, somatostatin, somatostatin octapeptide analog, cyclosporin, renin inhibitor, superoxide dismutase; other hormones; anti-coagulants, such as heparin or short chain heparin; and anti-migraine drugs.

Pharmaceutical agents also include OTC agents for cold/flu, allergies, etc.

The compounds can be administered orally, alone or in combination with additional therapeutics, to a subject in need of treatment. Thus, methods are provided comprising administering or prescribing any one of the delivery matrices or compositions thereof to a subject in need thereof, in an aspect. Formulations can include mixtures of any of the agents provided herein (e.g., natural products, OTC and/or pharmaceuticals). The administering can be a direct administration or can be indirect (e.g., directing a subject to ingest any one of the compositions provided herein).

Dosage regimens must be titrated to the particular indication, the age, weight, and general physical condition of the patient, and the response desired but generally doses will be from about 1 to about 1000 milligrams/day as needed in single or multiple daily administration.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient.

Unless otherwise specified herein, the amount (by weight) of a dose of a composition comprising at least one agent as well as the concentrations per vial provided herein refers to the amount or concentration of the therapeutic(s), respectively, not including the any added excipients in the composition. It should be understood that the amount provided herein can be an average amount based on a population of the respective molecules in a composition.

In some embodiments, any one of the subjects for treatment as provided in any one of the methods provided may have a nutritional deficiency and/or disease or disorder. In some embodiments, any one of the subjects for treatment as provided in any one of the methods provided the subject has had or is expected to have a nutritional deficiency.

The delivery systems provided herein may comprise further inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol) or comparable natural alternatives based on specific formulation objectives.

Compositions according to the invention may comprise pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, compositions are suspended in a sterile saline solution for injection together with a preservative.

It is to be understood that the compositions of the invention can be made in any suitable manner, and the invention is in no way limited to compositions that can be produced using the methods described herein. Selection of an appropriate method of manufacture may require attention to the properties of the particular elements being associated. In some embodiments, compositions are manufactured under sterile conditions or are initially or terminally sterilized. This can ensure that resulting compositions are sterile and non-infectious, thus improving safety when compared to non-sterile compositions. This provides a valuable safety measure, especially when subjects receiving the compositions have immune defects, are suffering from infection, and/or are susceptible to infection. In some embodiments, the compositions may be lyophilized and stored in suspension or as lyophilized powder depending on the formulation strategy for extended periods without losing activity.

The compositions of the invention can be administered in effective amounts, such as the effective amounts described elsewhere herein. Doses of compositions as provided herein may contain varying amounts of elements according to the invention. The amount of elements present in the compositions for dosing can be varied according to their nature, the therapeutic benefit to be accomplished, and other such parameters. The compositions for dosing may be administered according to any one of the frequencies provided herein.

"Amount effective" in the context of a composition or dose for administration to a subject refers to an amount of the composition or dose that produces one or more desired responses in the subject. In some embodiments, the amount effective is a pharmacodynamically effective amount. Any one of the compositions or doses as provided herein can be in an amount effective.

Doses of the components in any one of the compositions of the invention or used in any one of the methods of the invention may refer to the amount of the components in the composition, the actual amounts of the respective components received by an administered subject, or the amount that appears on a label. The dose can be administered based on the number of micron particles (and/or volume of the emulsion delivery system) that provide the desired amount of the agent(s).

Kits

Another aspect of the disclosure relates to kits. In some embodiments, the kit comprises any one or more of the compositions provided herein. The composition can be in any form provided herein. The composition(s) can be in in more than one container in the kit, for example the components may be kept separate until formation of the emulsion, fluid gel or hydrogel is desired. In some embodiments of any one of the kits provided, the container is a vial or an ampoule. In some embodiments of any one of the kits provided, the composition(s) are in lyophilized form each in a separate container or in the same container, such that they may be reconstituted at a subsequent time. In some embodiments of any one of the kits provided, the kit further comprises instructions for reconstitution, mixing, administration, ingestion, etc. In some embodiments of any one of the kits provided, the instructions include a description of any one of the methods described herein. Instructions can be in any suitable form, e.g., as a printed insert or a label.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different from illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The following description provides examples of the methods provided herein.

EXAMPLES

Example 1—Preparation of a Bioactive Gel

An exemplary method for preparing a bioactive gel (1000 gallon cGMP production run) is presented below. First, a premix 1 solution (the oil phase) was created in stainless steel tank with impeller mixer (A) using sunflower oil (Odyssey 100 High Stability >80% oleic acid) heated to 65° C. in a low shear propeller mixer while protected from light. Next, oil soluble Cytoguard OX-OST, vitamin E (d-alpha tocopheryl acetate from sunflower) in sunflower oil, beta-carotene (Lyc-O-Beta-Blakeslea trispora fungus dispersion in sunflower oil; pre-warmed and mixed at 65° C.), vitamin D3 (cholecalciferol) in medium-chain triglycerides (MCTs), vitamin A (as retinol palmitate), and vitamin K2-7 (10,000 PPM microencapsulated on maltodextrin) were each added in order to the sunflower oil, forming the oil phase. The mixture was kept at 65° C. with low shear propeller mixer throughout the additions and mixed for at least 15 minutes at 65° C. to create a homogenous oil phase. The oil phase remained protected from light.

In a separate 100 gallon tank with impeller mixer (B) pectin was hydrated by adding pectin powder (GENU® Pectin LM-104 AS-Z) and double-distilled water (ddH$_2$O) at room temperature with low shear propeller mixer. The mixture was heated to 80° C. for two hours to completely hydrate the powder, and then cooled to room temperature.

In a separate stainless steel tank 1000 gallon (batch tank with impeller mixer) the water phase was formed by adding lactic acid (Purac Fit Plus 90 Lactic Acid) and glycerin to ddH$_2$O at room temperature with low speed mixing using inline Silverson with General Purpose Mixing Head (1000 to 2000 RPM) and 100 gallon Likwifier Square Tank mixer to premix/hydrate ingredients prior to high shear mixing using inline Silverson mixer with General Purpose mixing heads. The resulting mixture was heated to 75° C. and maintained at 1000-2000 RPM mixing while the following ingredients were added sequentially (each ingredient was dissolved before the next ingredient was added): Cytoguard® water soluble OX-WST, potassium sorbate, *Quillaja saponaria* Molina saponin-rich tree bark extract (Q-Naturale 200V), monoammonium glycyrrhizinate MM100F, and water insoluble Vitamin C (as ascorbyl palmitate) to generate the water phase. The water phase was then maintained at 75° C. as a clear yellow solution. Note that if water phase is cooled below 60° C. the clear solution transitions to white milky opaque dispersion that will undergo phase transition and separation with visible crystalline glass-like particles. Emulsion will not optimally form if water phase is not clear yellow solution >65° C. when oil phase is added.

The oil phase (tank A) was slowly added to the water phase at 75° C. with high shear mixing (>5000 RPM) using inline Silverson Multipurpose Mixing Head. For smaller particles the Emulsor mixing head can be used. Once the oil phase was fully added to the water phase, the resulting orange emulsion (600 to 1200 nanometeres) was maintained at 75° C. with high shear (>5000 RPM). The heat was then turned off and immediately the hydrated pectin (at room temperature, tank B) was added. Purified water (ddH$_2$O) was then added at room temperature to decrease the time necessary to cool the mixture to 42° C.

Once the mixture reached 42° C., the following ingredients were added sequentially (e.g., each ingredient was allowed to dissolve before the subsequent ingredient was added): thiamin, B1 (Thiamine Mononitrate 33.3%; ROCOAT®), niacin (vitamin B3), riboflavin (vitamin B2; riboflavin-5-phosphate), D-biotin, iodine (as potassium iodide), chromium (dinicocysteinate; Zychrome®), selenium (as glycinate), molybdenum (as glycinate), vitamin B6 (pyridoxine HCl), vitamin B12 (adenosylcobalamin), vitamin B12 (methylcobalamin), blueberry extract, pomegranate extract color (FRUITMAX®), aronia juice concentrate.

At 42° C. ingredients containing divalent cations (specifically calcium and zinc) were added to induce gelation of the pectin with high shear mixing to form micron-sized fluid gel particles (1-10 microns). Standardized fruit blend (SFB, contains magnesium hydroxide and tri-calcium phosphate), pantothenic acid (vitamin B5, D-calcium pantothenate, 8.3% calcium), L-methylfolate (MagnaFolate-C™; 8% calcium), calcium (as lactate gluconate, 13%), magnesium (as gluconate, 5.05-5.8%; 5.5%), zinc (lactate), and manganese (glycerophosphate). Organic palmyra sugar (SugaVida™), lactic acid (Purac® Fit Plus 90 (0.15%)) potassium sorbate, natural blue color were added at 75° C. for taste, color and to prevent microbial growth. At this stage the red/purple liquid has the consistency of orange juice with fine pulp.

To increase viscosity gum acacia (Fibregum™), and beta-glucan (PROMOAT®) were added at 25-45° C. using high shear Silverson mixer with General Purpose Head (>4000 rpm). The resulting mixture was cooled to room temperature (22-30° C.). Then, the following ingredients were slowly added: Cytoguard® OX-WST (water soluble tea antioxidant), mixed berry flavor (28-05-0115), mixed berry flavor (30202), and vitamin C (ascorbic acid). Water loss due to evaporation of the batch was then adjusted with ddH$_2$O. The reddish purple viscous hydrogel at pH 3.5 to 4.2 was then subjected to nitrogen purge and did not undergo phase separation (−20° C. to 45° C.)

Example 2—Vegan Formulation

An exemplary method for synthesizing a vegan bioactive gel is presented below. First, a premix 1 solution (the oil phase) is created using ahiflower oil (Odyssey 100 High Stability) heated to 65° C. in a low shear mixer while protected from light. Next, Cytoguard OX-OST, vitamin E (d-alpha tocopherol acetate from sunflower) in sunflower oil, beta-carotene (Lyc-O-Beta-Blakeslea trispora fungus; pre-warmed and mixed at 65° C.), vitamin D3 (cholecalciferol) in medium-chain triglycerides (MCTs), vitamin A (as retinol palmitate), vitamin K1 oil, vitamin K2-7 (from vegetable source, 10,000 PPM powder), and bioperine are each added in order to the ahiflower oil, forming the oil phase. The mixture is kept at 65° C. with low shear throughout the additions, and the oil phase is low shear mixed for at least 15 minutes at 65° C. The oil phase remains protected from light.

The pectin hydration step includes mixing pectin (GENU® Pectin LM-104 AS-Z) and double-distilled water (ddH$_2$O) at room temperature with moderate shear. The mixture is heated to 80° C. during hydration, and then cooled to room temperature.

The water phase is formed as lactic acid (Purac Fit Plus 90 Lactic Acid), glycerin, and allulose syrup (ALLSWEET®) are added to ddH$_2$O at room temperature with low mixing (2500 RPM). The resulting mixture is heated to 75° C. and maintained at 2500 RPM mixing while the following ingredients are added sequentially (each ingredient is dissolved before the next ingredient is added): Cytoguard® OX-WST, potassium sorbate, *Quillaja* extract (Q-Naturale 200V), Glycyrrhizin monoammoniated MM100F, and Vitamin C (as ascorbyl palmitate) to generate the water phase. The water phase is then maintained at 75° C. as a clear yellow solution.

The oil phase is slowly added to the water phase at 75° C. with high shear (5000 RPM). Once the oil phase is fully added to the water phase, the resulting emulsion is maintained at 75° C. with high shear (5000 RPM). The heat is then turned off and the hydrated pectin (at room temperature) is added with high shear. Purified water (ddH$_2$O) is then added at room temperature to decrease the time necessary to cool the mixture to 42° C.

Once the mixture reaches 42° C., the following ingredients are added sequentially (e.g., each ingredient is allowed to dissolve before the subsequent ingredient is added): blueberry extract, niacin (vitamin B3), D-biotin, iodine (as potassium iodide), chromium (dinicocysteinate; Zychrome®), selenium (as glycinate), molybdenum (as glycinate), boron glycinate (Bororganic), vitamin B6 (pyridoxine HCl), vitamin B12 (adenosylcobalamin), vitamin B12 (methycobalamin), choline bitartrate, taurine, acetyl-L-carnitine, carnosine, creatine AH (creatine anhydrous), lysine hydrochloride, inositol vitamin B1 (thiamin, 33.3%, ROCOAT®), standardized fruit blend (SFB, non-GMO maltodextrin containing Ca/Mg), pantothenic acid (vitamin B5, D-calcium pantothenate, 8.3% calcium; 5 mg), L-methylfolate (MagnaFolate-C™; 8% calcium), calcium phosphate versacal clear (14.8%), zinc bisglycinate chelate (10%), marine magnesium (SIMAG 15, 12%), manganese bisglycinate chelate (18%), trace minerals fulvic (Ioniplex), short-chain fructooligosaccharide (NutraFlora P95), organic palmyra sugar (SugaVida™), betaine anhydrous, potassium sorbate, acacia gum (FIBREGUM®), and beta-glucan (PROMOAT®). The resulting mixture is cooled to room temperature. Then, the following ingredients are slowly added: Cytoguard® OX-WST (powder form), mixed berry natural flavor (28-05-0115, liquid), mixed berry natural flavor (30202, liquid), vitamin C (ascorbic acid), silica (ORGONO® living silica), microencapsulated reduced iron (Jostocote), microencapsulated cupric sulfate monohydrate copper (Jostocote, 50%), and thaumatin (Katemfe or Talin).

Example 3—Preparation of a Pharmaceutical Delivery System

An exemplary method for synthesizing a pharmaceutical delivery system is presented below. First, an oil phase solution is created using oil paired with a single active ingredient (drug, OTC, or purified nutraceutical) heated to 65° C. in a low shear mixer while protected from light. Examples of potential active ingredient-oil combinations include: rapamycin with ahiflower, sunflower, coconut medium-chain triglycerides (MCT) with lauric acid, or MCT oil, simvastatin (ZOCOR®) with ahiflower oil, lycopene (15% oil) with ahiflower oil, ibuprofen with ahiflower or MCT oil, ibuprofen sodium with ahiflower oil, and acetaminophen with ahiflower oil. Next, Cytoguard OX-OST, is added to the active ingredient-oil mix, forming the oil phase. The mixture is kept at 65° C. with low shear throughout the additions.

The water phase is formed as lactic acid (Purac Fit Plus 90 Lactic Acid) and glycerin are added to ddH$_2$O. The resulting mixture is heated to 75° C. and maintained at 2500 RPM mixing while the following ingredients are added sequentially (each ingredient is dissolved before the next ingredient is added): glycerin, Cytoguard® OX-WST (powder form), potassium sorbate (0.1005% final), *Quillaja* extract (Q-Naturale 200V), Glycyrrhizin monoammoniated MM100F, and Vitamin C (as ascorbyl palmitate) to generate the water phase. The water phase is then maintained at 75° C. as a clear yellow solution.

To generate the emulsion, the water and oil phase are mixed at high shear at 75° C. The emulsion may be complexed to pectin microbeads as follows.

The pectin hydration step includes mixing pectin (GENU® Pectin LM-104 AS-Z, 0.5%) and double-distilled water (ddH$_2$O) at room temperature with moderate shear. The mixture is heated to 80° C. during hydration, and then cooled to room temperature. The resulting pectin mixture is then slowly added to the emulsion at 75° C. and high shear (5000 RPM), and then cooled to 42° C. Once the mixture reaches 42° C., calcium (e.g., calcium phosphate versacal clear (14.8%), lactate gluconate, etc.) is added to induce gelation, and efficient and homogeneous complexation of O/W hydrogel emulsion to pectin. A viscous hydrogel can be prepared by adding beta glucan and acacia gum.

What is claimed is:

1. A dietary product or oral pharmaceutical comprising an oil-in-water (O/W) emulsion complex comprising a water phase and an oil phase, ascorbyl palmitate, a high hydrophile-lipophile balance (HLB) saponin with a HLB of greater than or equal to 10, and a *Glycyrrhiza glabra* (licorice) root saponin, wherein the concentration of ascorbyl palmitate is 0.15-4.5 mg/gm, wherein the concentration of the high HLB saponin is 0.01-1.6 mg/gm, and wherein the concentration of *Glycyrrhiza glabra* root saponin is 0.02-160 mg/gm.

2. The dietary product or oral pharmaceutical of claim 1, wherein the high HLB saponin is a *Quillaja saponaria* saponin.

3. The dietary product or oral pharmaceutical of claim 1, wherein the high HLB saponin is a *Yucca saponin*.

4. The dietary product or oral pharmaceutical of claim 1, wherein the high HLB saponin is from tea seeds, bitter melon *Momordica charantia*, *Panax ginseng*, fenugreek *Trigonella Foenum graecum*, alfalfa root *Medicago sativa*, Siberian ginseng *Eleuthrerococcus senticosus*, *Astragalus membranaceus*, *Bacopa monniera*, *Nigella sativa*, *Aralia mandshurica*, *Beyonia alba*, *Rhaponticum carthamoides*, *Gymnema sylvestre*, *Gynostemma pentaphyllum*, *Withania somnifera*, *Tinaspora cordifolia*, Milkwort *Polygala*, *Simlax officinalis*, or *Aesculis hipocastanum*.

5. The dietary product or oral pharmaceutical of claim 1, wherein the *Glycyrrhiza glabra* (licorice) root saponin is monoammonium glycyrrhizinate, ammoniated glycyrrhizin, or glycyrrhizic acid.

6. The dietary product or oral pharmaceutical of claim 1, wherein the oil phase comprises an edible oil.

7. The dietary product or oral pharmaceutical of claim 1, wherein the O/W emulsion complex further comprises a stabilizing hydrophilic agent, wherein the stabilizing hydrophilic agent is a cyclodextrin, maltodextrin, beta glucan, dietary fiber, natural emulsifier protein, or cationic carrier.

8. The dietary product or oral pharmaceutical of claim 1, wherein the O/W emulsion complex further comprises a compound that increases bioavailability, wherein the compound that increases bioavailability is a fructooligosaccharide, dietary fiber, mucilaginous extract, hydrocolloid, quercetin, ginger, genistein, naringin, sinomenine, piperine, nitrile glycoside, beta glucan, or chitosan.

9. The dietary product or oral pharmaceutical of claim 1, wherein the O/W emulsion complex further comprises a viscosity modifier, a humectant, mucilaginous ingredient, plant extract, dietary fiber, protein, cyclodextrin, pectin, polyethylene glycol, propylene glycol, alcohol, cold set plant extract, agar, starch, cellulose gum, locust bean gum, hydrocolloid, polyvinylpyrrolidone, poloxamer 488, carboxymethylcellulose, gum acacia, or beta glucan.

10. A dietary product or oral pharmaceutical comprising a gel delivery matrix comprising:

(a) an O/W emulsion complex that is thixotropic with a glass-transition temperature range between 50-80° C.;

(b) a pectin with 10-40% ester groups; and (c) a cation, wherein the concentration of pectin is 1-10 mg/gm or.

11. A dietary product or oral pharmaceutical comprising a hydrogel delivery matrix comprising:

(a) gel delivery matrix or an O/W emulsion complex that is thixotropic with a glass-transition temperature range between 50-80° C.;

(b) at least one beta glucan; and (1) any one or more of acacia gum, a hydrocolloid, and a molecule that reduces syneresis and increases viscosity; and/or (2) a fructooligosaccharide and/or mucilaginous extract, hydrocolloid, or dietary fiber;

wherein the molecule that reduces syneresis and increases viscosity is a plant extract, dietary fiber, protein, cyclodextrin, beet pectin or high methoxy calcium insensitive pectin, or cold set plant extract, and wherein the concentration of the beta glucan is 2-30 mg/gm.

12. The dietary product or oral pharmaceutical of claim 1, wherein the O/W emulsion complex has a glass-transition temperature range between 50-80° C.

13. The dietary product or oral pharmaceutical of claim 1, wherein the O/W emulsion complex further comprises a dietary agent.

14. The dietary product or oral pharmaceutical of claim 1, wherein the O/W emulsion complex further comprises a pharmaceutical agent.

15. The dietary product or oral pharmaceutical of claim 10, wherein the pectin is an amidated pectin.

16. The dietary product or oral pharmaceutical of claim 10, wherein the pectin comprises the structure as shown in FIG. 1:

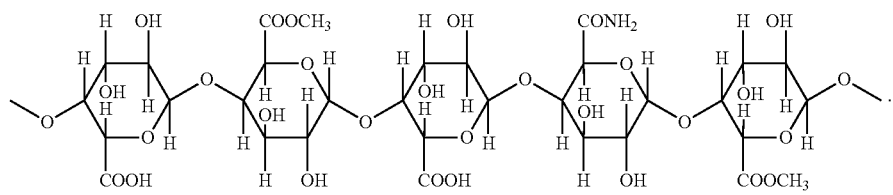

(Fig. 1)

17. The dietary product or oral pharmaceutical of claim 10, wherein the cation is a divalent cation.

18. The dietary product or oral pharmaceutical of claim 17, wherein the divalent cation is a Calcium, Zinc, Magnesium or Manganese divalent cation.

19. The dietary product or oral pharmaceutical of claim 10, wherein the gel delivery matrix has a viscosity of 50-50,000 cps.

20. The dietary product or oral pharmaceutical of claim 11, wherein the hydrogel delivery matrix comprises acacia gum, and wherein the concentration of the acacia gum is 2-30 mg/gm.

21. The dietary product or oral pharmaceutical of claim 11, wherein the hydrogel delivery matrix has a viscosity of 10,000 to 100,000 cps.

22. The dietary product or oral pharmaceutical of claim 11, wherein the gel delivery matrix is the gel delivery matrix of claim 10.

23. The dietary product or oral pharmaceutical of claim 10, wherein the concentration of pectin is 1.5-5 mg/gm.

24. The dietary product or oral pharmaceutical of claim 10, wherein the O/W emulsion complex is the O/W emulsion complex of claim 1.

25. The dietary product or oral pharmaceutical of claim 10, wherein the pectin is citrus peel pectin.

26. The dietary product or oral pharmaceutical of claim 10, wherein the pectin is apple pectin.

* * * * *